United States Patent
El-Moaty et al.

(10) Patent No.: US 11,975,038 B1
(45) Date of Patent: May 7, 2024

(54) THERAPEUTIC COMPOSITION INCLUDING PHENOLIC COMPOUNDS DERIVED FROM OPUNTIA LITTORALIS

(71) Applicant: KING FAISAL UNIVERSITY, Al-Ahsa (SA)

(72) Inventors: Heba Ibrahim Abd El-Moaty, Al-Ahsa (SA); Hairul-Islam Mohamed Ibrahim, Al-Ahsa (SA); Zainab Hussain Almansour, Al-Ahsa (SA); Rabab Salem Hamad, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/226,572

(22) Filed: Jul. 26, 2023

Related U.S. Application Data

(62) Division of application No. 18/125,106, filed on Mar. 22, 2023, now Pat. No. 11,806,378.

(51) Int. Cl.
*A61K 47/10* (2017.01)
*A61K 9/107* (2006.01)
*A61K 36/36* (2006.01)

(52) U.S. Cl.
CPC .............. *A61K 36/36* (2013.01); *A61K 9/107* (2013.01); *A61K 47/10* (2013.01)

(58) Field of Classification Search
None
See application file for complete search history.

(56) References Cited

FOREIGN PATENT DOCUMENTS

| JP | 01277475 | * | 11/1989 |
| KR | 20020072130 | * | 2/2002 |
| KR | 101932089 B1 | | 12/2018 |

OTHER PUBLICATIONS

How does oxidative stress affect the body?, Medical News Today, accessed Nov. 20, 2023 . (Year: 2023).*
El-Moaty et al. (Structural elucidation of phenolic compounds isolated from Opuntia littoralis and their antidiabetic, antimicrobial and cytotoxic activity, South African Journal of Botany 131 (2020) 320-327. (Year: 2020).*
Almansour et al., "Phenolic-Compound-Rich Opuntia littoralis Ethyl Acetate Extract Relaxes Arthritic Symptoms in Collagen-Induced Mice Model via Bone Morphogenic Markers," Nutrients. Dec. 17, 2022;14(24):5366.
Abd el Moaty et al., "Structural elucidation of phenolic compounds isolated from Opuntia littoralis and their antidiabetic, antimicrobial and cytotoxic activity," South African Journal of Botany, vol. 131, Jul. 2020, pp. 320-327.*

* cited by examiner

*Primary Examiner* — Melissa S Mercier
(74) *Attorney, Agent, or Firm* — Nath, Goldberg & Meyer; Richard C. Litman

(57) ABSTRACT

A therapeutic composition including phenolic compounds derived from *Opuntia littoralis* (OL) includes an extract of *Opuntia littoralis* and lutein. The *Opuntia littoralis* extract can be formed by extracting an *Opuntia littoralis* plant powder with an alcohol to provide an *Opuntia littoralis* alcohol extract (OLAE) including the phenolic compounds. In an embodiment, the therapeutic composition can be effectively used as an analgesic for the treatment of pain, as an anti-inflammatory, as a treatment for immunological disorders, and/or as a treatment for oxidant conditions.

5 Claims, 3 Drawing Sheets

THERAPEUTIC COMPOSITION INCLUDING PHENOLIC COMPOUNDS DERIVED FROM OPUNTIA LITTORALIS

CROSS-REFERENCE TO RELATED APPLICATION

This application is a divisional of U.S. patent application Ser. No. 18/125,106, filed on Mar. 22, 2023.

BACKGROUND

1. Field

The disclosure of the present patent application relates to antioxidant and anti-inflammatory compositions and, more particularly, to compositions including phenolic compounds derived from *Opuntia littoralis*.

2. Description of the Related Art

Therapeutic preparations which are based on natural ingredients can frequently provide relief for several ailments at once. Different species of plants, for example, contain nutrients and compounds that are useful for various human health issues. For this reason, many plants are typically used for treating cosmetic or medical conditions. Cacti plants, in particular, are considered a rich source of a variety of beneficial nutrients and compounds.

*Opuntia littoralis* is a species of prickly pear cactus known by the common name coastal prickly pear. Prickly pear is high in fiber, antioxidants, and carotenoids. The edible parts of prickly pear include the fruit, stems, leaves, and flowers.

Thus, a therapeutic composition including phenolic compounds derived from *Opuntia littoralis* solving the aforementioned problems is desired.

SUMMARY

A therapeutic composition including phenolic compounds derived from *Opuntia littoralis* (OL) includes an alcoholic extract of *Opuntia littoralis* and lutein. The *Opuntia littoralis* extract can be formed by extracting an *Opuntia littoralis* plant powder with an alcohol to provide an *Opuntia littoralis* alcohol extract (OLAE) including the phenolic compounds. In an embodiment, the therapeutic composition can be effectively used as an analgesic for the treatment of pain and as anti-inflammatory. In an embodiment, the therapeutic composition can be useful for treating immunological disorders. In an embodiment, the therapeutic composition can provide therapeutic use in the treatment of oxidant conditions.

A pharmaceutical composition can include a therapeutically effective amount of the therapeutic composition and a pharmaceutically acceptable carrier or excipient. In some embodiments, the present compositions can be used for combination therapy, where other therapeutic and/or prophylactic ingredients can be included therein.

A process for the preparation of the therapeutic composition can include providing a plant part of OL, reducing the plant part to a powder, and extracting the OL with water and alcohol to obtain an OL alcohol extract (OLAE), which comprises the phenolic acids and flavonoids of OL molecules. The plant powder can be formed by drying the *Opuntia littoralis* plant or plant part, e.g., cladode and fruits, and reducing the dried plant or plant part to a powder. The plant powder can be extracted from the part of the *Opuntia littoralis* plant with 70% aqueous ethanol over multiple days, for example, 8 days. The OLAE can be mixed with an emulsified lutein homogenate to provide an emulsion.

These and other features of the present subject matter will become readily apparent upon further review of the following specification.

BRIEF DESCRIPTION OF THE DRAWINGS

(FIG. 1B) lutein-treated cells; and (FIG. 1C) OLAE and lutein-treated cells.

DETAILED DESCRIPTION OF THE PREFERRED EMBODIMENTS

Figure 1A:
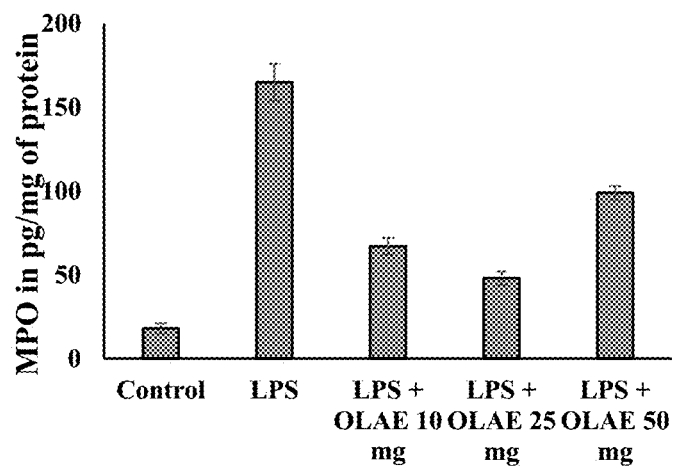
FIGS. 1A-1C are graphs showing oxidative stress in LPS induced RAW 264.7 cell lines estimated based on the activity of MPO in μM/mg of (FIG. 1A) OLAE-treated cells.

The following definitions are provided for the purpose of understanding the present subject matter and for construing the appended patent claims.

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an inflammatory condition or an immunological disorder.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present disclosure is related to a therapeutic composition including phenolic compounds derived from *Opuntia littoralis* (OL). In an embodiment, the therapeutic composition includes an alcoholic extract of *Opuntia littoralis* and lutein. In an embodiment, the therapeutic composition can include from about 0.1 gram to about 1 gram of *Opuntia littoralis* and about 1 mM to about 10 mM lutein. The therapeutic composition can be effectively used to treat at least one condition selected from pain, inflammation, an immunological disorder, and an oxidant condition.

In an embodiment, the therapeutic composition can include an *Opuntia littoralis* alcohol extract (OLAE). The OLAE can be prepared by preparing a plant powder from a part of the *Opuntia littoralis* plant. In an embodiment, the part of the *Opuntia littoralis* plant or plant part includes at least one of a fruit and a cladode of the *Opuntia littoralis* plant. The plant part can be dried and reduced to a plant powder. The plant powder can be extracted with an alcohol such as ethanol. In an embodiment, the plant powder can be combined with 70% aqueous ethanol over multiple days to obtain the OLAE. In certain embodiments, the plant powder can be combined with the aqueous ethanol once, twice, three times, four times, five times, or more for a period of two, three, four, five, six, seven, eight, nine, ten, or more days to provide a residue. In an embodiment, the plant powder can be combined with the aqueous ethanol four times for a period of about eight days to provide a residue. Any inorganic salts and non-phenolic compounds can be removed from the residue to provide the OLAE.

According to an embodiment, a method of preparing the therapeutic composition can include combining the extract of *Opuntia littoralis* with an emulsified lutein homogenate. In an embodiment, the extract of *Opuntia littoralis* is OLAE. In an embodiment, the emulsified lutein homogenate can be prepared by mixing a lutein powder with stearic acid.

A process for the preparation of OL phenolic compounds can include providing a plant part of OL, reducing the plant part to a powder, and extracting the OL with water and alcohol to obtain an OL alcohol extract (OLAE). The OLAE can be mixed with an emulsified lutein homogenate to provide an emulsion including the phenolic acids and flavonoids of OL. In an embodiment, the present subject matter relates to a therapeutic composition produced according to the present synthesis methods.

The therapeutic composition can have more than one therapeutic use. In an embodiment, the therapeutic composition can be effectively used as an analgesic for the treatment of pain. In an embodiment, the therapeutic composition can be effectively used as an anti-inflammatory. In an embodiment, the therapeutic composition can be useful for treating immunological disorders. In an embodiment, the therapeutic composition provides antioxidant activity as well as therapeutic use in the treatment and management of pain and inflammatory conditions.

In some embodiments, the present compositions can be used for combination therapy, where other therapeutic and/or prophylactic ingredients can be co-administered therewith.

A pharmaceutical composition can include the therapeutic composition and a pharmaceutically acceptable carrier or excipient. Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. In an embodiment, a therapeutically effective amount of the therapeutic composition can include from about 0.01 mg to 500 mg per unit dose. For example, a therapeutically effective amount of the therapeutic composition can include from about 1 mg to about 100 mg per unit dose.

The present compounds are typically administered at a therapeutically or pharmaceutically effective dosage, e.g., a dosage sufficient to provide treatment for an immunological disease or an inflammatory disorder. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, the pharmaceutical composition can include about 0.01 mg to 500 mg of the therapeutic composition per unit dose, for example about 1 mg to about 100 mg per unit dose. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present composition for treatment of pain, immune disorders, oxidant conditions, and/or inflammatory conditions, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in immediate, sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as a "dietary supplement" or a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect.

In an embodiment, the pharmaceutical composition may be in the form of an immediate-release, controlled-release, or sustained-release orally administrable composition for a pill, tablet, capsule, gelcap, lozenge, throat spray, solution, emulsion, cream, paste, gel, cough drop, or dissolvable strip. In an embodiment, the pharmaceutical composition may be in the form of a liquid solution, liquid spray, emulsion, cream, gel, lotion, or impregnated dressing.

In an embodiment, the pharmaceutical composition may in the form of nasal drops, oral drops, eye drops, or aerosol trigger.

The present teachings are illustrated by the following examples.

Example 1

Preparation of Opuntia littoralis Alcohol Extract (OLAE)

Two kilos of the dried plant powder were extracted with 70% aqueous ethanol four times for 8 days. The obtained greenish sticky residue was dissolved in water, treated with excess of ethanol and filtered to remove inorganic salts and non-phenolic compounds. The alcoholic extract was evaporated under reduced pressure at 50° C. until dry.

Example 2

Preparation of Therapeutic Composition

A lutein enriched extract preparation was prepared by mixing lutein powder (Pure Tru Herb Private Limited) with stearic acid to provide an emulsified mixture or emulsified lutein homogenate including an amount of 1 mM to 10 mM lutein. The emulsified lutein homogenate was mixed with the alcoholic extract (0.1 g to 1 g) of Opuntia littoralis. The mixture was reduced by sonicating for 90 seconds using a pulse sequence that consisted of 25% alcoholic extract with different concentrations of lutein (Fisher Scientific, Madison, WI, USA). The emulsion was used for in vitro and in vivo analysis.

Example 3

Myeloperoxidase (MPO) Quantification

Figure 1B:
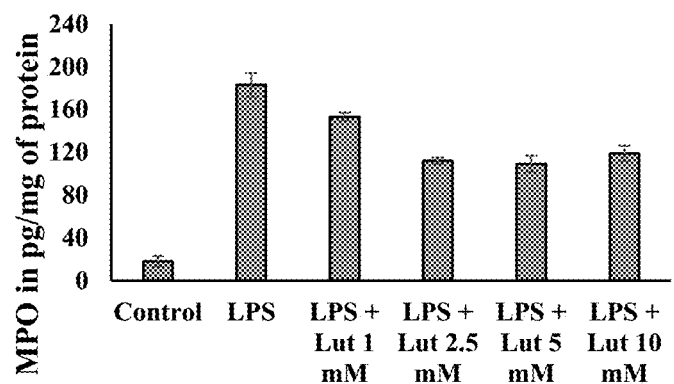
Figure 1C:
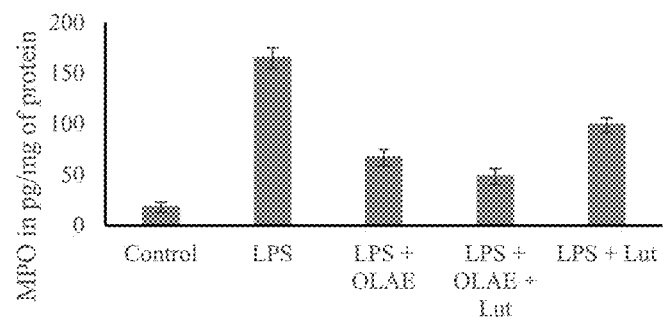

The expression of oxidative stress in lipopolysaccharide (LPS)-induced RAW 264.7 cell lines was estimated. The activity of Myeloperoxidase (MPO), a marker of neutrophilic infiltration, and the nitrite levels in µM/mg of OLAE treated cells were determined according to the method described in Hairul et al., 2021. Briefly, lipopolysaccharide (LPS)-induced RAW cells were homogenized using lysate buffer (Invitrogen, Waltham, Massachusetts, USA). Cell-free lysate was separated using centrifugation. The absorbance was recorded using a spectrophotometer at 512 nm (Thermo scientific, Waltham, Massachusetts, USA). FIGS. 1A-1C show results of this analysis. MPO activity was expressed as units per milligram of wet tissue. One unit expresses the MPO activity needed for the conversion of 1 mM of $H_2O_2$ to water in 1 min at room temperature. The intensity of color modification was modified based on levels of free lipid peroxidation in the samples.

Example 4

Cytotoxic Activity

Figure 2:
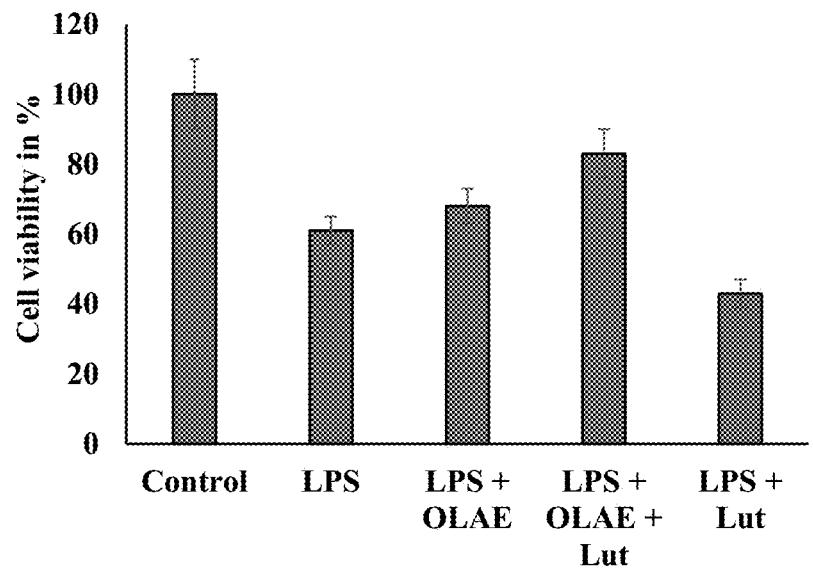
FIG. 2 is a graph showing cytotoxicity measured by SRB assay of *O. littoralis* alcohol extract OLAE (25 μg/mL), Lut (2.5 μM) treatment, and the therapeutic composition according to the present teachings.

Potential cytotoxicity was measured by SRB assay of the different concentrations of the cladode extracts of O. littoralis alcohol extract OLAE (25 µg/mL) and Lutein (2.5 µM) treatment, by the method described by Skehan et al. (1990) using a murine macrophage cell line. FIG. 2 is a graph showing cell viability of the different concentrations of the cladode extracts of O. littoralis alcohol extract OLAE (25 µg/mL) and Lutein. The intensity of color was inversely proportional to cell viability and was measured using an ELISA reader (450 nM). A plot of the relation between survival fraction and dry concentration was designed to get the survival curve of each tumor cell line after the extract treatment.

Example 5

Nitric Oxide (NO) Quantification

Figure 3:
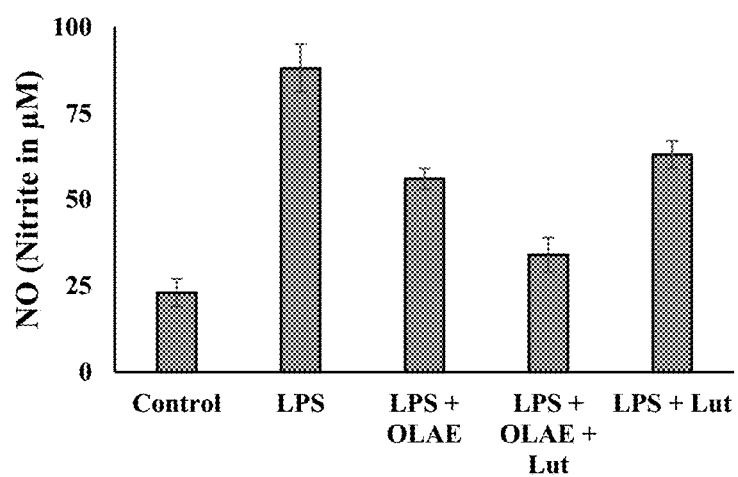
FIG. 3 is a graph shows Nitric Oxide (NO) in OLAE-treated, lutein-treated, and OLAE and lutein-treated limb tissue.

The expression of oxidative stress and the nitrite levels in limb tissue were estimated. The nitrite levels in µM/mg of tissue were determined according to the method in (Khalifa et al., 2022). Briefly, the LPS-induced cells were homogenized using lysate buffer (Invitrogen, Waltham, Massachusetts, USA). Cell-free lysate was separated using centrifugation 8000 g rpm. The absorbance was recorded using a spectrophotometer at 512 nm (Thermo scientific, Waltham, Massachusetts, USA). MPO activity was expressed as units per milligram of wet tissue. For NO quantification, the homogenate of the above-mentioned samples was mixed with Griess reagent, and the color intensity of the Griess reagent was modified based on levels of free nitrates in the samples. The results of this analysis are summarized in FIG. 3.

Example 6

Cell-Invasion Assay (Transwell-Assay)

Figure 4:
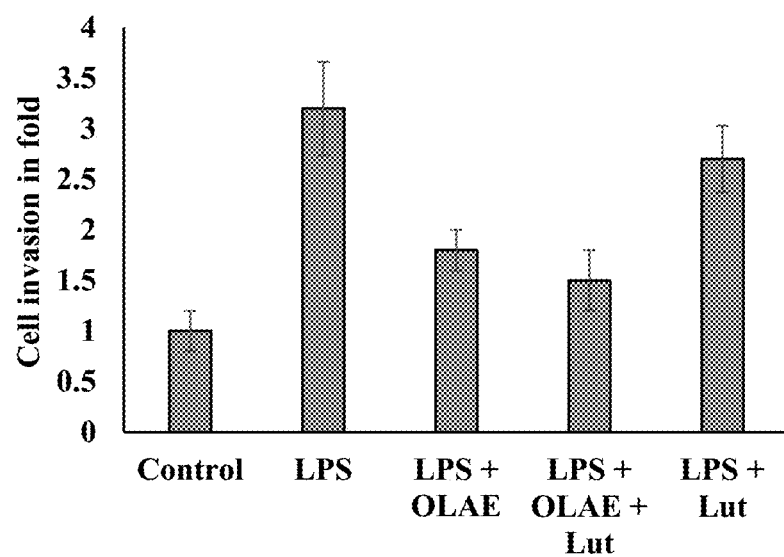
FIG. 4 is a graph showing cell invasion assessed using transwell cell culture Boyden chambers seeded with OLAE (25 μg/mL), lutein (2.5 μM), OLAE plus lutein, and 100 μL of MDA cells ($5\times10^4$).

Cell invasion was assessed using transwell cell culture Boyden chambers, according to the manufacturer's protocol. Gelatin coated 12-well plate cell culture inserts (BD Biosciences) were used with a polyethylene terephthalate membrane (8-μm porosity) and the inserts were incubated for 6 h at 37° C. Before OLAE (25 μg/mL) and Lutein (2.5 μM) treatment, 100 μL of MDA cells ($5 \times 10^4$) were seeded in the upper chamber in serum-free media treated with OLAE and Lutein at the indicated concentrations and 700 μL of DMEM medium supplemented with 10% FBS was added to the lower chamber. The cells were then incubated for 24 h at 37° C. Then, the remaining cells on the top surface of the membrane were removed using a cotton swab, and the cells on the bottom of the membrane were fixed in cold methanol (75%) for 15 min and washed with PBS three times. Afterward, the cells were stained with Giemsa (30%) staining solution and washed with PBS. Then, cells in five randomly selected fields were counted under a light microscope at 20× objective magnification. The number of migrated cells was tallied by optical microscopy (magnification: 200×) and manual counting. All assays were performed in triplicate. The results are summarized in FIG. 4.

It is to be understood that the therapeutic composition including phenolic compounds derived from *Opuntia littoralis* is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A method of providing antioxidant activity in a subject, comprising:
    administering a therapeutically effective amount of a pharmaceutical composition to a subject in need thereof;
    wherein the pharmaceutical composition comprises a therapeutic composition and a pharmaceutically acceptable carrier or excipient; and
    wherein the therapeutic composition includes phenolic compounds derived from *Opuntia littoralis*, comprising:
        an alcoholic extract of *Opuntia littoralis*; and
        lutein.
2. The method of claim 1, wherein about 0.01 mg to about 500 mg of the therapeutic composition is administered per unit dose.
3. The method of claim 1, wherein about 1 mg to about 100 mg of the therapeutic composition is administered per unit dose.
4. The method of claim 1, wherein the therapeutic composition comprises:
    from about 0.1 gram to about 1 gram of the alcoholic extract of *Opuntia littoralis*; and
    from about 1 mM to about 10 mM of lutein.
5. The method of claim 1, wherein the therapeutic composition comprises about 1 mg to about 100 mg of lutein per unit dose.

* * * * *